(12) United States Patent
Johnson et al.

(10) Patent No.: US 10,596,358 B2
(45) Date of Patent: Mar. 24, 2020

(54) DEVICES AND METHODS FOR INTRALUMINAL RETENTION AND DRUG DELIVERY

(71) Applicant: PALO ALTO RESEARCH CENTER INCORPORATED, Palo Alto, CA (US)

(72) Inventors: David Mathew Johnson, San Francisco, CA (US); Martin Sheridan, Redwood City, CA (US); Scott A. Uhland, San Jose, CA (US); Ramkumar Abhishek, Mountain View, CA (US); Eric Peeters, Mountain View, CA (US); Timothy J. Curley, San Carlos, CA (US); Felicia Linn, San Jose, CA (US); Philipp H. Schmaelzle, Los Altos, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 275 days.

(21) Appl. No.: 15/658,172

(22) Filed: Jul. 24, 2017

(65) Prior Publication Data
US 2017/0319834 A1 Nov. 9, 2017

Related U.S. Application Data

(62) Division of application No. 13/742,203, filed on Jan. 15, 2013, now Pat. No. 9,744,341.

(51) Int. Cl.
*A61M 31/00* (2006.01)
*A61D 7/00* (2006.01)
*A61M 5/145* (2006.01)

(52) U.S. Cl.
CPC ............. *A61M 31/002* (2013.01); *A61D 7/00* (2013.01); *A61M 5/1452* (2013.01); *A61M 2210/1433* (2013.01); *A61M 2210/1475* (2013.01)

(58) Field of Classification Search
CPC ............. A61M 31/002; A61M 5/1452; A61M 31/005; A61M 25/04; A61M 2025/0286
See application file for complete search history.

(56) References Cited

U.S. PATENT DOCUMENTS

| | | |
|---|---|---|
| 3,561,438 A | 2/1971 | Canel |
| 3,590,816 A | 7/1971 | Rosenthal |

(Continued)

FOREIGN PATENT DOCUMENTS

| | | |
|---|---|---|
| DE | 4130843 A1 | 3/1993 |
| WO | 1994/01165 A1 | 1/1994 |

(Continued)

OTHER PUBLICATIONS

Fatakdawala, Hussain et al., "Hydrogen peroxide mediated transvaginal drug delivery," International Journal of Pharmaceutics 409 (2011) 121-127.

(Continued)

*Primary Examiner* — Nathan R Price
*Assistant Examiner* — Melissa A Snyder
(74) *Attorney, Agent, or Firm* — Shun Yao; Park, Vaughan, Fleming & Dowler LLP

(57) ABSTRACT

Retention devices and methods are provided for drug delivery. The device may include a housing configured for intraluminal deployment into a human or animal subject and at least one reservoir contained within the housing. The at least one reservoir may have an actuation end and a release end and contain at least one drug formulation. A plug may be contained within the at least one reservoir and be move- (Continued)

able from the actuation end toward the release end. The device may also include an actuation system operably connected to the actuation end of the at least one reservoir and configured to drive the at least one drug formulation from the reservoir. The device may also include at least one retention member affixed to the housing and movable between a non-stressed position, a deployment position, and a retention position for retaining the device in an intraluminal location in the subject.

21 Claims, 12 Drawing Sheets

(56) References Cited

U.S. PATENT DOCUMENTS

| | | | |
|---|---|---|---|
| 3,807,395 | A | 4/1974 | Chaft |
| 3,902,501 | A * | 9/1975 | Citron .................. A61N 1/057 607/126 |
| 4,202,329 | A | 5/1980 | Kortum |
| 4,304,232 | A | 12/1981 | Michaels |
| 4,308,867 | A | 1/1982 | Roseman et al. |
| 4,402,695 | A | 9/1983 | Wong |
| 4,687,423 | A | 8/1987 | Maget et al. |
| 4,886,514 | A | 12/1989 | Maget |
| 4,902,278 | A | 2/1990 | Maget et al. |
| 5,002,540 | A | 3/1991 | Brodman et al. |
| 5,062,834 | A | 11/1991 | Gross et al. |
| 5,090,963 | A | 2/1992 | Gross et al. |
| 5,112,614 | A | 6/1992 | Magruder et al. |
| 5,135,499 | A | 8/1992 | Tafani et al. |
| 5,267,960 | A * | 12/1993 | Hayman ............... A61N 5/1027 600/3 |
| 5,318,557 | A | 6/1994 | Gross |
| 5,354,264 | A | 10/1994 | Bae et al. |
| 5,415,629 | A | 5/1995 | Henley |
| 5,522,804 | A | 6/1996 | Lynn |
| 5,593,552 | A | 1/1997 | Joshi et al. |
| 5,780,058 | A | 7/1998 | Wong et al. |
| 5,816,248 | A | 10/1998 | Anderson et al. |
| 5,928,195 | A | 7/1999 | Malamud et al. |
| 5,951,538 | A | 9/1999 | Joshi et al. |
| 6,030,375 | A | 2/2000 | Anderson et al. |
| 6,086,909 | A | 7/2000 | Harrison et al. |
| 6,139,538 | A | 10/2000 | Houghton et al. |
| 6,183,434 | B1 | 2/2001 | Eppstein |
| 6,322,532 | B1 | 11/2001 | D'Sa et al. |
| 6,352,524 | B1 | 3/2002 | Bunt et al. |
| 6,423,039 | B1 | 7/2002 | Rathbone et al. |
| 6,444,224 | B1 | 9/2002 | Rathbone et al. |
| 6,450,991 | B1 | 9/2002 | Bunt et al. |
| 6,532,386 | B2 | 3/2003 | Sun et al. |
| 6,591,133 | B1 | 7/2003 | Joshi |
| 6,638,246 | B1 | 10/2003 | Naimark et al. |
| 6,756,053 | B2 | 6/2004 | Zhang et al. |
| 6,776,164 | B2 | 8/2004 | Bunt et al. |
| 6,805,877 | B2 | 10/2004 | Massara et al. |
| 6,835,392 | B2 | 12/2004 | Hsu et al. |
| 6,962,579 | B2 | 11/2005 | Jellie |
| 6,978,172 | B2 | 12/2005 | Mori et al. |
| 7,004,171 | B2 | 2/2006 | Benita et al. |
| 7,083,590 | B1 | 8/2006 | Bunt et al. |
| 7,486,989 | B2 | 2/2009 | Sun et al. |
| 7,497,855 | B2 | 3/2009 | Ausiello et al. |
| 7,732,408 | B2 | 6/2010 | Josephson et al. |
| 9,005,108 | B2 | 4/2015 | Uhland et al. |
| 9,055,959 | B2 * | 6/2015 | Vaska ................ A61B 17/2202 |
| 2002/0010414 | A1 | 1/2002 | Coston et al. |
| 2002/0045883 | A1 | 4/2002 | Jellie |
| 2003/0018295 | A1 | 1/2003 | Henley et al. |
| 2003/0130558 | A1 | 7/2003 | Massara et al. |
| 2003/0219472 | A1 | 11/2003 | Pauletti et al. |
| 2004/0059388 | A1 | 3/2004 | Herbst et al. |
| 2004/0082937 | A1 | 4/2004 | Ausiello et al. |
| 2004/0087893 | A1 | 5/2004 | Kwon |
| 2004/0219192 | A1 | 11/2004 | Horstmann et al. |
| 2005/0054969 | A1 | 3/2005 | Hoff et al. |
| 2005/0124875 | A1 | 6/2005 | Kawano et al. |
| 2005/0244502 | A1 | 11/2005 | Mathias et al. |
| 2005/0267440 | A1 | 12/2005 | Herman et al. |
| 2006/0024358 | A1 | 2/2006 | Santini et al. |
| 2006/0184092 | A1 | 8/2006 | Atanasoska et al. |
| 2007/0038181 | A1 | 2/2007 | Melamud et al. |
| 2007/0225634 | A1 | 9/2007 | Ferren et al. |
| 2007/0269435 | A1 | 11/2007 | Yun et al. |
| 2008/0004564 | A1 | 1/2008 | Smith |
| 2008/0004596 | A1 | 1/2008 | Yun et al. |
| 2008/0262412 | A1 | 10/2008 | Atanasoska et al. |
| 2008/0269666 | A1 | 10/2008 | Wang et al. |
| 2009/0131737 | A1 | 5/2009 | Ferren et al. |
| 2009/0171315 | A1 | 7/2009 | Versi |
| 2009/0306633 | A1 | 12/2009 | Trovato et al. |
| 2009/0312833 | A1 | 12/2009 | Tittelbach |
| 2011/0087155 | A1 | 4/2011 | Uhland et al. |
| 2011/0087192 | A1 | 4/2011 | Uhland et al. |
| 2011/0087195 | A1 * | 4/2011 | Uhland ............... A61M 37/0015 604/515 |
| 2011/0251660 | A1 * | 10/2011 | Griswold ........... A61N 1/37205 607/126 |
| 2013/0211372 | A1 | 8/2013 | Rosenshein |
| 2014/0088345 | A1 | 3/2014 | Uhland et al. |
| 2014/0088486 | A1 | 3/2014 | Uhland et al. |

FOREIGN PATENT DOCUMENTS

| | | |
|---|---|---|
| WO | 1994/18952 A1 | 9/1994 |
| WO | 1997/41831 A1 | 11/1997 |
| WO | 2001/12101 A1 | 2/2001 |
| WO | 2005/056708 A2 | 6/2005 |
| WO | 2005/089728 A2 | 9/2005 |
| WO | 2007/041119 A1 | 4/2007 |
| WO | 2007/047811 A2 | 4/2007 |
| WO | 2007/140416 A2 | 12/2007 |
| WO | 2009/081411 A2 | 7/2009 |
| WO | 2010/048478 A2 | 4/2010 |

OTHER PUBLICATIONS

Sáfilho, O. G. et al., "Fixed-time artificial insemination with estradiol and progesterone for Bos indicus cows II: Strategies and factors affecting fertility," Science Direct, Theriogenology 72 (2009) 210-218.

* cited by examiner

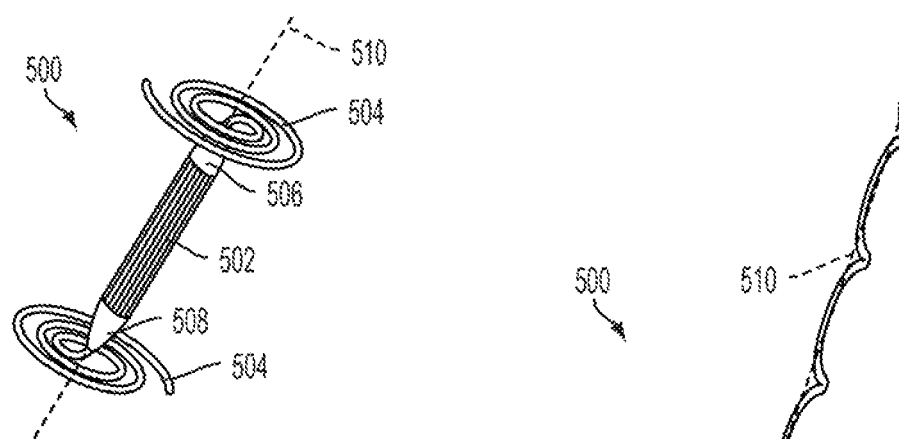
FIG. 5A
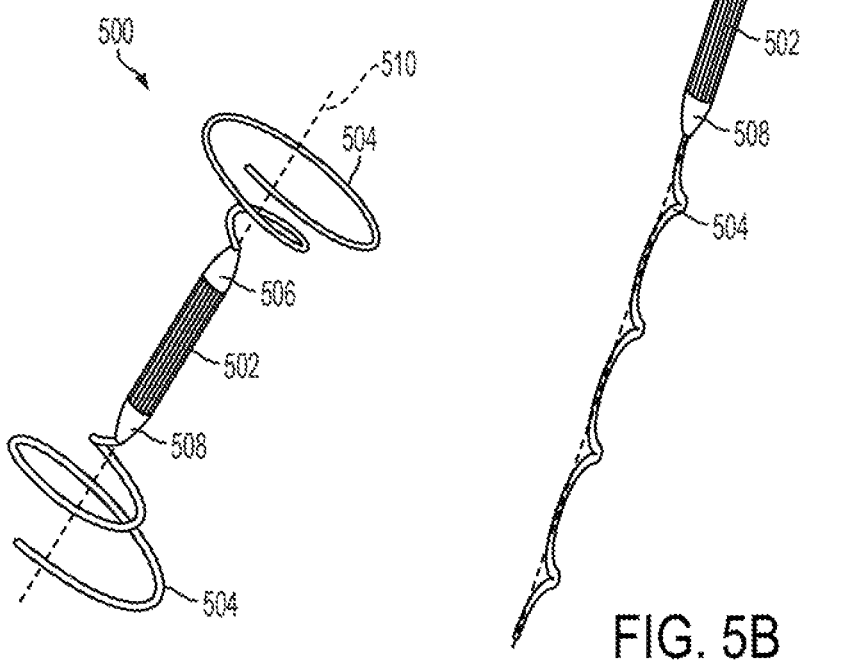
FIG. 5B
FIG. 5C

DEVICES AND METHODS FOR INTRALUMINAL RETENTION AND DRUG DELIVERY

CROSS REFERENCE TO RELATED APPLICATIONS

This application is a divisional of U.S. application Ser. No. 13/742,203, filed Jan. 15, 2013, which is incorporated herein by reference in its entirety.

FIELD

The present disclosure is generally in the field of drug delivery devices and methods, and more particularly is related to intraluminal deployment and retention of drug delivery devices in human and animal subjects for delivery of drug from the intraluminally retained device.

BACKGROUND

Controlled delivery of multiple drugs from a single device is an area of interest because of the potential of delivering a series of drugs in a treatment regimen in a specific release profile. For example, current fixed time artificial insemination (FTAI) treatments for cattle require the administration of multiple drugs at specific times. These treatments result in significant time spent driving, herding, and chuting the cattle, cause stress and increased cortisol levels in the subjects, and require multiple drug delivery devices and precise drug administration timing.

Transmucosal drug delivery is an area of interest because of the potential of delivering systemically-acting drugs with a high relative bioavailability by avoiding first-pass metabolism effects, the potential of locally delivering therapeutic agents to a site of interest, and the convenience of application routes. Some of the possible sites for transmucosal drug delivery include the buccal, nasal, vaginal, and rectal administration routes. In many of these delivery methods, it is important that the inserted device be retained at the intended intraluminal insertion site for an extended period of time, typically while the subject maintains its usual levels of activity. In various embodiments, the means of retention should be reliable and relatively easy to use, and it should be relatively easy for the physician, subject, or others to remove the intraluminal device at the appropriate time. There is thus a need to provide improved means of deploying and retaining such intraluminal drug delivery devices.

SUMMARY

In one aspect, a device for drug delivery is provided, which includes a housing configured for intraluminal deployment into a human or animal subject, at least one drug reservoir in the housing, and at least one retention member affixed to the housing and movable between a non-stressed position, a deployment position, and a retention position for retaining the device in an intraluminal location in the subject. The at least one drug reservoir contains at least one drug formulation. The at least one reservoir may have an actuation end and a release end and include a plug within the at least one reservoir, wherein the plug is moveable from the actuation end toward the release end. The device also may include an actuation system operably connected to the actuation end of the at least one reservoir and configured to drive the at least one drug formulation from the reservoir.

In another aspect, an intraluminal device is provided that includes a tubular housing and a retention sleeve that has at least two arms, each arm having a first end and a second end. The first ends are affixed to the housing and the second ends are affixed to a ring positioned about the housing and slideable between a deployment position in which the at least two arms are adjacent the housing and a retention position in which the at least two arms are outwardly expanded.

In yet another aspect, a method of drug delivery is provided, which includes transforming a retention member operably associated with a device from a non-stressed position into a deployment position, deploying the device into a mucosal lumen of a human or animal subject, transforming the retention member from the deployment position into a retention position, and then actuating an actuation system to drive a drug from one or more reservoirs in the device. In one embodiment, the device includes a tubular housing and a retention sleeve having at least two arms, each arm having a first end and a second end, the first ends being affixed to the housing and the second ends being affixed to a ring positioned about the housing, and the transforming step includes sliding the ring to outwardly expand the at least two arms of the retention sleeve into a retention position.

BRIEF DESCRIPTION OF THE DRAWINGS

FIGS. 5A-5C are perspective views, illustrating one embodiment of a drug delivery device having a retention member.

DETAILED DESCRIPTION

The devices and methods described herein provide for the storage and controlled delivery of drug formulations. The devices are advantageously configured to be deployed, and provide retention of the device, in a mucosal lumen of human or animal subjects in a manner that is reliable and facilitates relatively easy deployment and retrieval. In embodiments, the retention feature may permit or augment well targeted release of the drug to local mucosal or regional tissues of interest. The devices and methods are particularly suited for providing multiple doses of drug, which may be released intermittently over an extended period of in vivo deployment.

In one embodiment, the devices and methods may desirably allow for precise dispensing of drug formulations according to a specific release timing profile, which may significantly increase the accuracy and efficiency of delivering multiple agents to subjects. Such configurations may be particularly advantageous, for example, in large scale animal husbandry operations, such as artificial insemination.

The drug delivery device with retention feature may be provided in a number of different forms. It generally includes a housing (which holds the drug and other components) that is configured for intraluminal deployment into a human or animal subject. The term "animal subject" generally refers to mammalian subjects, including but not limited to bovine, ovine, equine, and porcine.

The term "intraluminal," as used herein, refers to placement within a body cavity, channel, tube, or the like, having a mucosal wall. The term includes, but is not limited to, intravaginal, intrauterine, and intragastrointestinal tract (e.g., rectal) sites.

Figure 9:
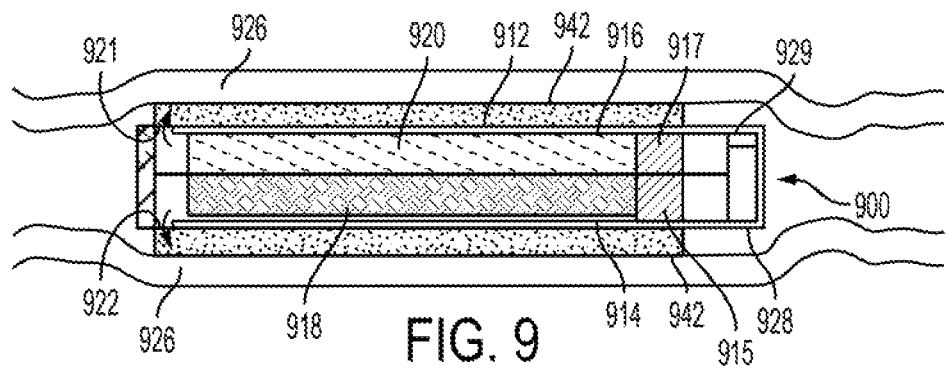
FIG. 9 is a cross-sectional view, illustrating one embodiment of a drug delivery device having two reservoirs.

The drug can be stored and released from the device housing in a variety of different ways. One embodiment is illustrated in FIG. 9. Here, the device 900 may include at least one reservoir 914, 916 contained within the housing 912. Each reservoir has an actuation end and a release end and contains at least one drug formulation 918, 920. The device also includes a plug 915, 917 within each reservoir, the plug being moveable from the actuation end toward the release end. An actuation system 929 is operably connected to the actuation end of each reservoir and is configured to device the at least one drug formulation 918, 920 from the reservoir 914, 916.

Figure 1A:
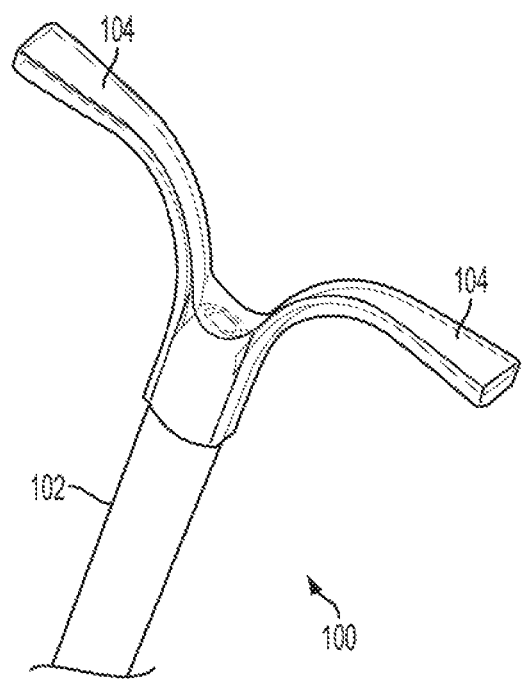
FIG. 1A is a perspective view, illustrating one embodiment of a drug delivery device having a retention member.
Figure 7:
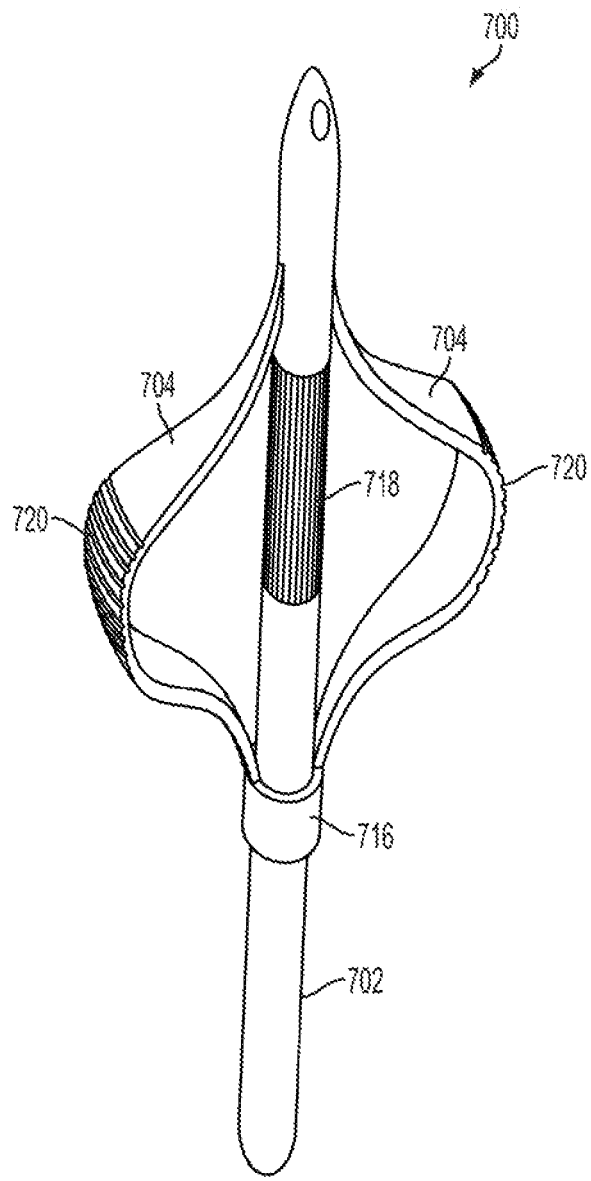
FIG. 7 is a perspective view, illustrating one embodiment of a drug delivery device having a retention sleeve.

FIG. 1A illustrates how a retention feature may be operably associated with such a drug delivery device housing. Here, luminal retention members 104 are affixed to the housing 102 and movable between a non-stressed position, a deployment position, and a retention position for retaining the device in an intraluminal location in the subject. FIG. 7 illustrates another way in which a retention feature may be operably associated with such a drug delivery housing. Here, the device 700 includes a tubular housing 702 and a retention sleeve that includes at least two arms 704, each arm having a first end and a second end, the first ends being affixed to the housing 702 and the second ends being affixed to a ring 716 positioned about the housing and slideable between a deployment position in which the at least two arms are adjacent the housing and a retention position in which the at least two arms are outwardly expanded.

Various embodiments and features of the drug delivery devices and methods are described in greater detail hereinafter.

Housing

Figure 8A:
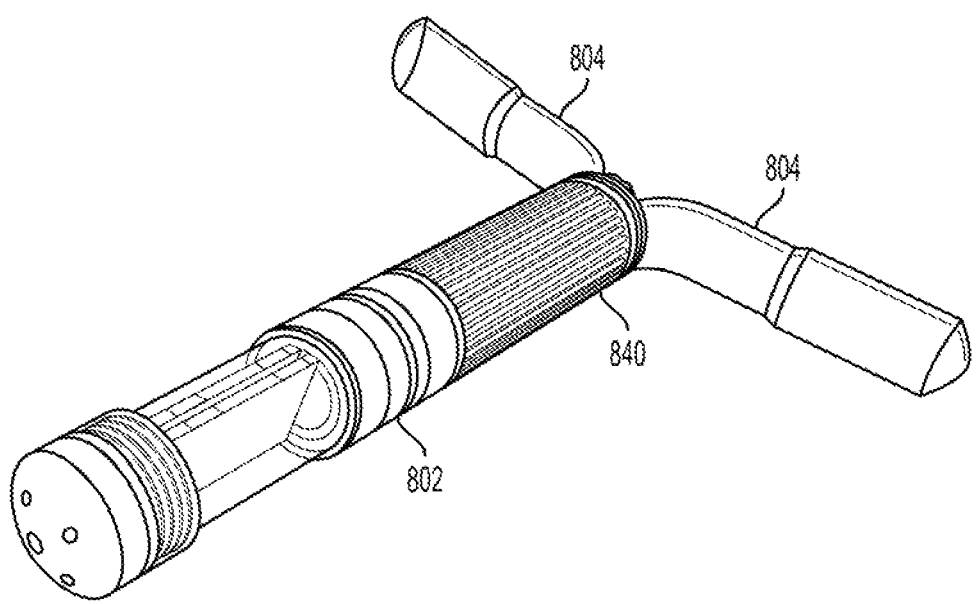
FIG. 8A is a perspective view, illustrating one embodiment of a drug delivery device having a retention member.

The device includes a housing generally configured to facilitate deployment of the drug delivery device within a lumen of a human or animal subject. The housing configuration is based upon the particular lumenal site and human or animal anatomical considerations, for deployment with minimal discomfort to the subject. In certain embodiments, the device may be placed within the lumen by insertion into the lumen via an exterior body orifice. Accordingly, in certain embodiments, the housing is shaped and dimensioned to allow insertion and placement, i.e., deployment, of the device within the intended lumen via the exterior body orifice. For example, the housing may be shaped and dimensioned for vaginal, cervical, uterine, or rectal insertion and placement. As shown in FIGS. 7 and 8A, the housing 702 and 802, respectively, may include an elongated, substantially cylindrical portion. These configurations may be suitable for vaginal device deployment in livestock, such as cattle, sheep, etc.

The materials of construction, size, shape, surface features, and other characteristics of the housing are configured such that the device can be deployed into the lumen, retained securely in the lumen during operation of the device, and retrieved from the lumen following operation of the device or when otherwise desired to be removed. For example, the housing may be tubular and have a cross-section that is substantially circular. In one embodiment, the housing is an elongated tube having an oval cross-section.

For example, the device may be removed between the delivery of individual drug formulations, following the delivery of several drug formulations, or following the completion of a course of treatment of multiple drug formulations. The device may be deployed until the drug formulation payload is depleted.

The housing may be formed of any biocompatible material. Moreover, the housing material may be resistant to degradation in the mucosal environment of the lumen. Examples of suitable housing materials include stainless steel, titanium, and polymers, ceramics or a composite of one of these materials. Alternatively, the housing may be formed of a biodegradable material, which will not substantially degrade until drug delivery is at least substantially complete. The housing material may include a coating to enhance biocompatibility and/or operation of the device.

Figure 10A:
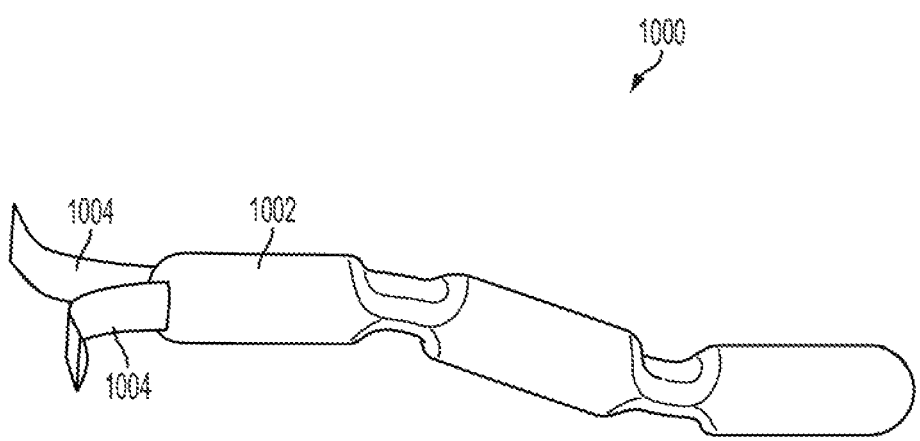
FIG. 10A is a perspective view, illustrating one embodiment of a drug delivery device having a retention member.
Figure 10B:
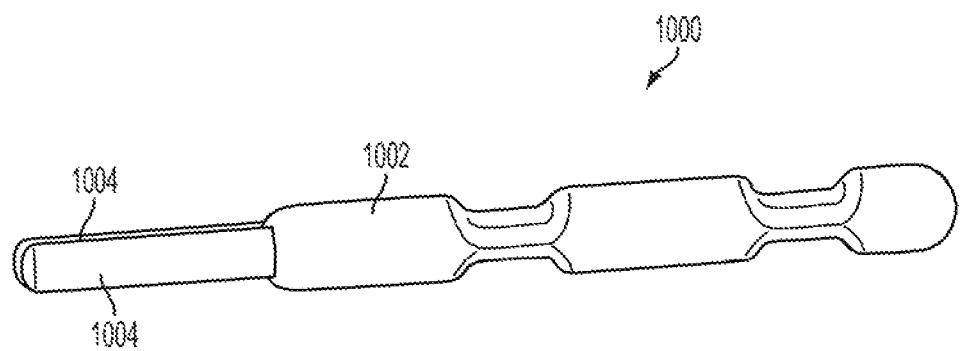
FIG. 10B is a perspective view, illustrating the drug delivery device of FIG. 10A in a deployment position.

In certain embodiments, as shown in FIGS. 10A and 10B, the housing 1002 is pliant at one or more points such that in the non-stressed position the housing 1002 is not straightened, as in FIG. 10A, and in the deployment position the housing 1002 is straightened, as in FIG. 10B.

Reservoirs and Contents

At least one reservoir is contained within the device housing. In an embodiment, the reservoir has an actuation end operably connected to an actuation system, as well as a release end. For example, each reservoir may be defined by an inner surface of an elongated annular tube. The reservoir may also have a shape similar to that of the housing and be configured such that it occupies a majority of the volume of the housing. In certain embodiments, the reservoir is elongated and has a circular cross-sectional shape. Other cross-sectional shapes are also envisioned.

The release end of the reservoir may include at least one outlet for releasing the drug formulations to the lumenal tissue. One end of the reservoir may be connected to the actuation end and the opposite end may include an outlet such as an aperture or nozzle. Multiple outlets may also be provided.

Each reservoir contains at least one drug formulation. The device may include one, two, or more than two drug formulations within each reservoir. For example, the reservoir may contain three or four drug formulations. The device may have one, two, three, or four reservoirs, with each reservoir containing at least one drug formulation. In one embodiment, each reservoir contains a drug that is different from the drug that is contained in the other reservoir(s). In particular embodiments, the multiple drugs are ones selected to work in concert, but beneficially are administered in series, for example in a separated or overlapping schedule. For example, the device may include multiple reservoirs as described in U.S. patent application Ser. No. 13/629,159, entitled "Multiple Reservoir Drug Delivery Device and Methods," or a single reservoir as described in U.S. patent application Ser. No. 13/629,124, entitled "Single Channel, Multiple Drug Delivery Device and Methods," the disclosures of which are incorporated herein by reference in their entirety.

In an embodiment, the reservoir also includes a plug which is movable from the actuation end of the reservoir toward the release end of the reservoir, wherein the plug is configured to drive the drug formulations, and any barriers therebetween, out of the reservoir. The plug generally is positioned between the actuation system and the drug formulations. The plug may include a fluid layer or a solid barrier.

Release Structure

The devices generally are configured to deliver the one or more drug formulations to the mucosal tissue of the lumen in which the device is deployed. The drug formulations may be released from at least one outlet at the release end portion of the reservoir, toward which the plug drives the drug formulations. The release end portion of the reservoir may be configured to release the drug formulations from the device axially, radially, or a combination thereof. In certain embodiments, the device includes a structure interposed between the at least one outlet and the tissue lumen. Such structures may function to redirect or spread the drug formulation across a greater area of the tissue lumen and/or may function to control release kinetics of the drug. For example, the device may include a porous membrane configured to diffuse the drug formulations released from the at least one outlet to the lumenal tissue.

Figure 8B:
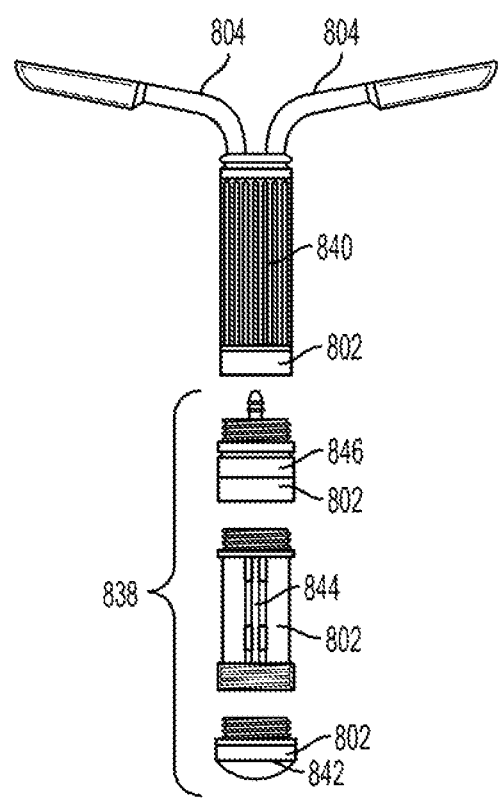
FIG. 8B is a partially exploded plan view, illustrating the drug delivery device of FIG. 8A.
Figure 8C:
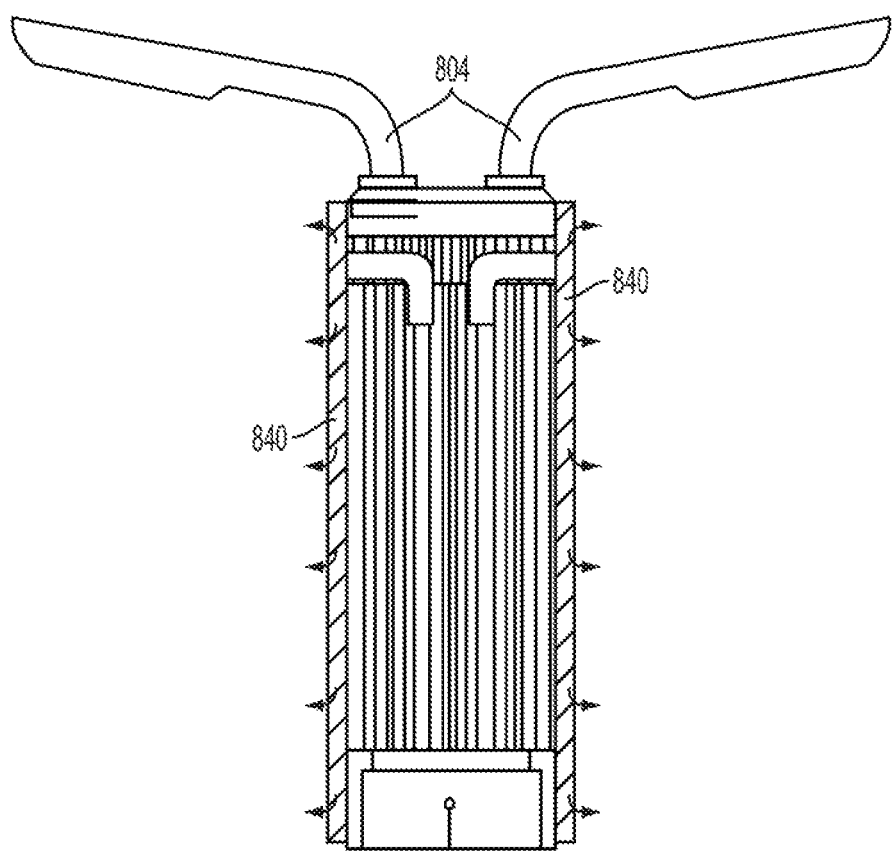
FIG. 8C is a partial cross-sectional view, illustrating the drug delivery device of FIGS. 8A-8B.

In certain embodiments, as shown in FIGS. 8A-8C, the housing 802 includes a porous membrane sidewall 840 in fluid communication with the release end of the reservoir. In certain embodiments, as shown in FIG. 7, at least a portion of the retention structure, for example arms 704, includes a porous membrane 720 in fluid communication with the release end of the at least one reservoir. The porous membrane may be configured to distribute the at least one drug formulation driven from the at least one reservoir to a tissue area adjacent the porous membrane while the device is deployed in the human or animal subject. For example, the porous membrane sidewall may diffuse the drug formulations over a region of the tissue membrane adjacent thereto. For example, the porous membrane sidewall may include a polycarbonate, polypropylene, PFTE, or polyethylene membrane, or a combination of laminates thereof. In an embodiment, the porous sidewall membrane has a pore size from about 0.2 micrometers to about 25 micrometers. The porous membrane sidewall may be as described in U.S. patent application Ser. No. 13/629,159, entitled "Multiple Reservoir Drug Delivery Device and Methods," the disclosure of which is incorporated herein by reference in its entirety.

In one embodiment, a ring of outlets is provided at the release end of the reservoir. For example, a ring of outlets may be radially positioned at the release end portion of a cylindrical reservoir. As shown in FIG. 9, outlets 921, 922 are radially positioned at the release end of reservoirs 914, 916. The outlets 921, 922 are in fluid communication with porous membrane sidewall 942.

Retention Structure

In certain embodiments, the drug delivery device includes at least one retention member affixed to the housing and movable between a non-stressed position, a deployment position, and a retention position for retaining the device in an intraluminal location in the subject. The retention member may include one or more arms reversibly extendable from the device housing. The arms may be elastically flexible, in whole or in part. In certain embodiments, the at least one retention member is in substantially the same position in the deployment position and the retention position.

Figure 1B:
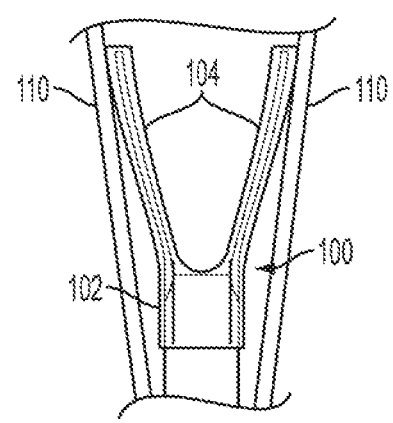
FIG. 1B is a plan view, illustrating the drug delivery device of FIG. 1A deployed and retained in a lumen.

As shown in FIGS. 1A-1B, the device 100 includes a drug reservoir housing 102 and a luminal retention member that includes two flexible arms 104 that are substantially perpendicular to the housing in the non-stressed position, as shown in FIG. 1A, substantially parallel to the housing in the deployment position, and in a position between the non-stressed and deployment positions in the retention position, as shown in FIG. 1B. For example, the at least two flexible arms may be configured to be deformed from the non-stressed position to the deployment position upon intraluminal deployment. The at least two flexible arms may also be configured to be deformed from the deployment position to the retention position after intraluminal deployment.

For example, the arms may be injection molded as part of the device housing or the porous membrane sidewall. The arms may be covered with a soft polymer through a secondary coating process or overmolding process. The arms may be configured to deform in response to intraluminal forces. For example, the arms may be plastically or elastically deformed. The device may be removed by pulling on the device, effective to overcome the frictional forces retaining the device in the lumen and/or to deform the arms into another position.

Figure 2A:
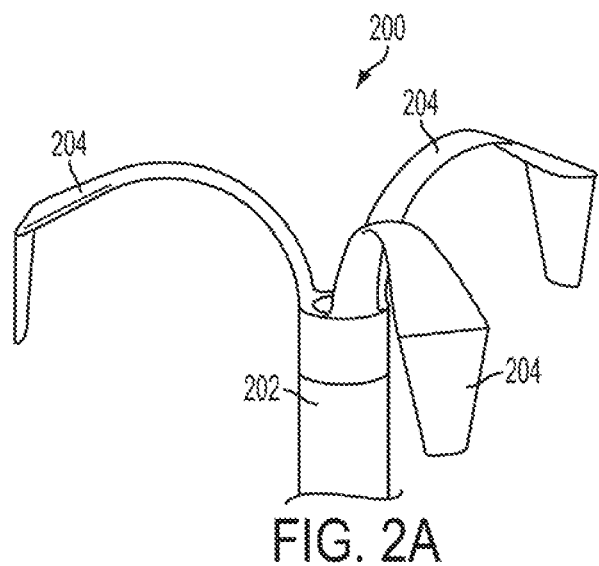
FIG. 2A is a perspective view, illustrating one embodiment of a drug delivery device having a retention member.
Figure 2B:
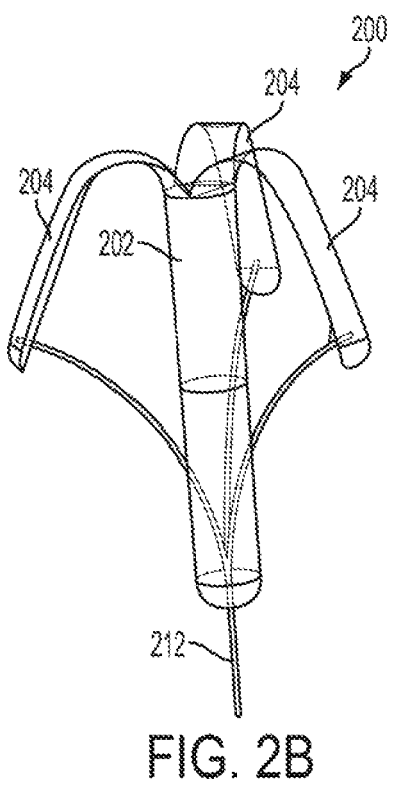
FIG. 2B is a plan view, illustrating the drug delivery device of FIG. 2A in a deployment position.

As shown in FIGS. 2A-2B, the retention member includes three arms 204, each having a first end and a second end, the first end being affixed to the housing 202 and the second end being distal the housing in the non-stressed position, as shown in FIG. 2A, and proximal the housing in the deployment position, as shown in FIG. 2B. In the retention position, the second ends of the arms 204 press against the tissue wall of the lumenal cavity in a position between the non-stressed position and the deployment position. For example, each arm 204 may be a flexible arcuate arm configured to be deformed from the non-stressed position to the deployment position upon intraluminal deployment. The arm 204 may also be configured to be deformed from the deployment position to the retention position after intraluminal deployment. For example, any force exerted on the arms may be translated to the device and cause the device to move farther into the lumen.

In certain embodiments, as shown in FIG. 2B, the device 200 includes a removal cord 212 connected to the second ends of the arms 204 and configured to move the second end of the arms 204 toward the housing 202 upon pulling the removal cord. The removal cord may be routed through a passageway in the center of the device. For example, the removal cord may be configured to be manually pulled by the subject or by a physician to move the retention member into a retention or deployment position. Alternatively, the removal cord may be configured to be pulled by an actuation system on board the device. For example, a microcontroller may be pre-programmed to pull the removal cord at a certain time after deployment or in response to a certain detected condition.

Figure 3A:
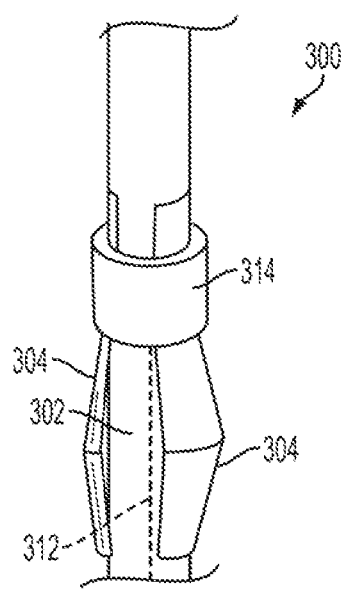
FIG. 3A is a plan view, illustrating one embodiment of a drug delivery device having a retention member.
Figure 3B:
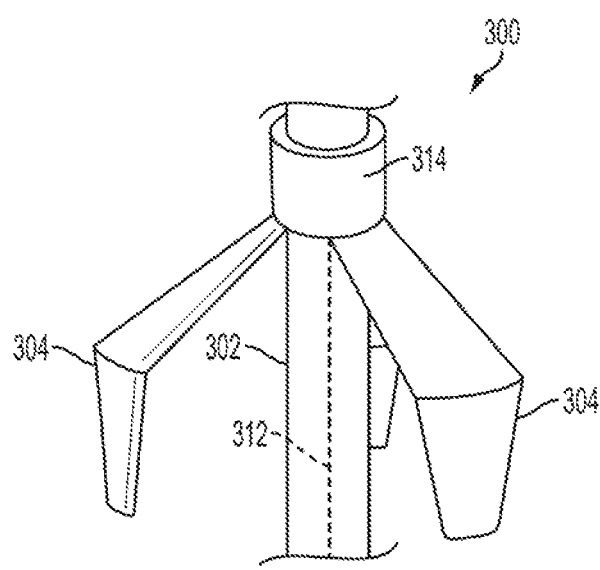
FIG. 3B is a plan view, illustrating the drug delivery device of FIG. 3A in a retention position.
Figure 3C:
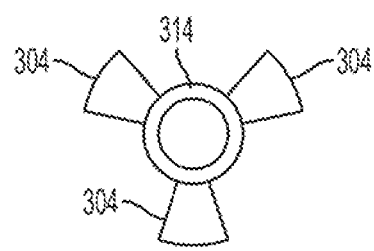
FIG. 3C is an end view, illustrating the drug delivery device of FIG. 3A.

In certain embodiments, as shown in FIGS. 3A-3C, the device 300 also includes a sleeve 314 positioned about the housing 302 and configured to be slideable axially along the housing and about the arms 304 such that the arms 304 assume a retracted or deployment position, as shown in FIG. 3A, adjacent the housing 302 when the sleeve 314 is slid from the first ends of the arms 304 toward the second ends of the arms 304. In one embodiment, the device also includes a removal cord 312 connected to the sleeve 314 and configured to slide the sleeve 314 about the arms 304 and move the arms 304 from the deployment position, as shown in FIG. 3A, to the non-stressed position, as shown in FIG. 3B, to facilitate insertion and removal of the device 300. While the devices illustrated in FIGS. 2A-B and FIGS. 3A-B have three arms, it is envisioned that the devices could instead have fewer or more arms, such as two, four, or five arms.

Figure 4A:
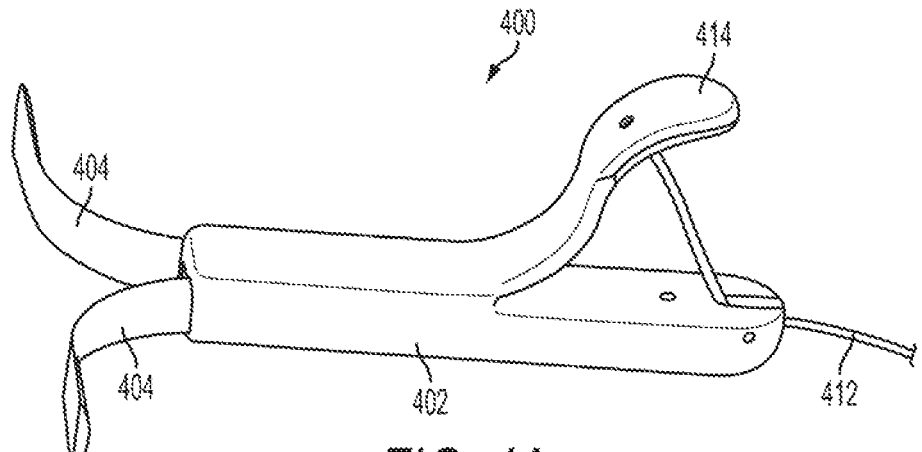
FIG. 4A is a perspective view, illustrating one embodiment of a drug delivery device having a retention member.
Figure 4B:
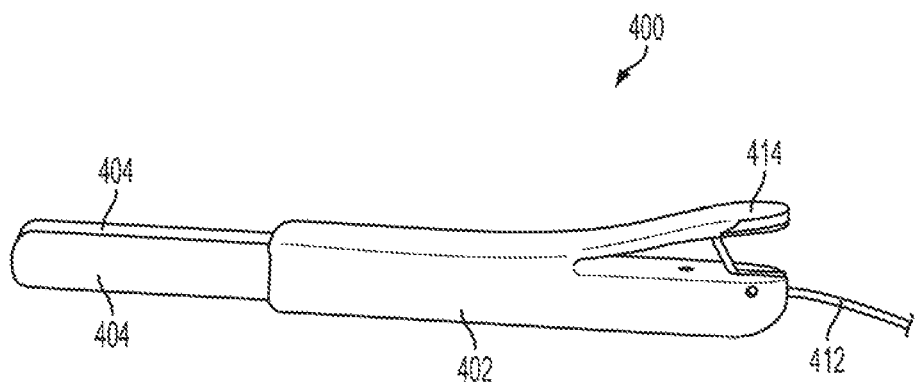
FIG. 4B is a perspective view, illustrating the drug delivery device of FIG. 4A in a deployment position.

In certain embodiments, as shown in FIGS. 4A and 4B, the retention member includes two flexible arms 404 that are substantially perpendicular to the housing 402 in the non-stressed position, as shown in FIG. 4A, and substantially parallel to the housing 402 in the deployment position, as shown in FIG. 4B. In addition, the retention member includes a third arm 414 at an opposing end of the housing 402 from the two flexible arms 404. The third arm 414 may be configured to exert a force on a portion of the lumen such that a portion of the housing is expanded or positionally adjusted to press against a wall of the lumen in the retention position. Cord 412 may be connected to the third arm 414 to provide for the retraction of the third arm 414 and the deformation of the third arm 414 from the deployment to the retention and/or non-stressed positions.

Figure 6A:
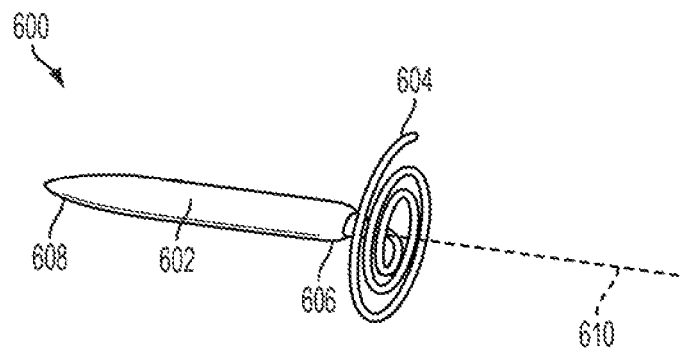
FIGS. 6A-6C are perspective views, illustrating one embodiment of a drug delivery device having a retention member.
Figure 6B:
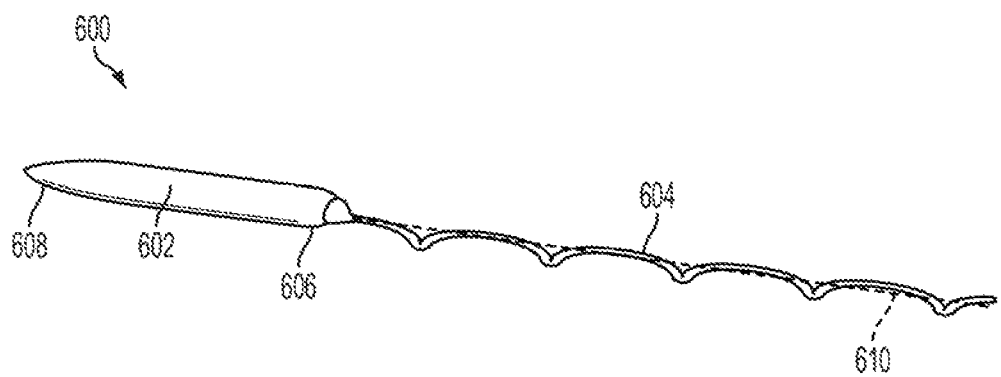
Figure 6C:
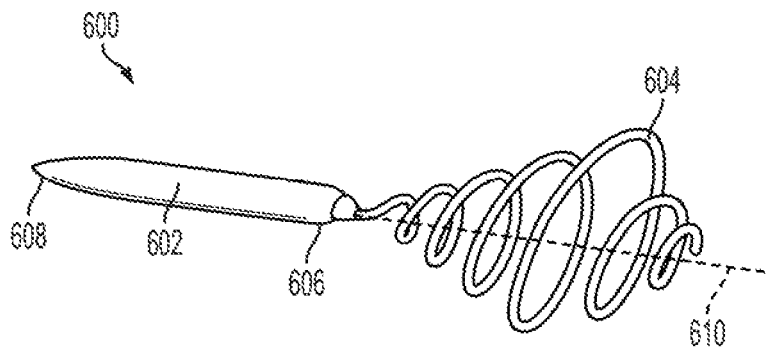

In certain embodiments, as shown in FIGS. 5A-5C and 6A-6C, the retention member comprises a spiral member 504, 604 having a first end and a second end, the first end being affixed to the housing 502, 602 and the second end being distal to the housing 502, 602. For example, the spiral member 504, 604 may have an axis and be affixed to the housing such that the axis is parallel to the longitudinal axis of the housing 502, 602. The device 500, 600 may be configured to be intraluminally deployed in a lumen of the human or animal subject by twisting the device such that the spiral member 504, 604 exerts a spring force against walls of the lumen in the retention position. In certain embodiments, the spiral member 504, 604 is configured to be straightened to facilitate deployment. In certain embodiments, the spiral member 504, 604 is configured such that a twisting motion of the device facilitates insertion and removal. The spiral may be substantially planar or it may be a three-dimensional spiral as shown in FIGS. 5A-5C and 6A-6C. In certain embodiments, as shown in FIGS. 5A-5C and 6A-6C, the housing 502, 602 has an actuation end 506, 606 and a release end 508, 608. In certain embodiments, as shown in FIGS. 5A-5C and 6A-6C, the retention member is movable between a non-stressed position (FIGS. 5A, 6A), a deployment position (FIGS. 5B, 6B), and a retention position (FIGS. 5C, 6C).

In certain embodiments, as shown in FIG. 7, the drug delivery device 700 includes a tubular housing 702 and a retention sleeve having two arms 704, each arm having a first end and a second end. Other numbers of arms are also envisioned. The first ends are affixed to the housing 702 and the second ends are affixed to a ring 716 positioned about the housing and slideable between a deployment position in which the two arms are adjacent the housing and a retention position in which the two arms are outwardly expanded. For example, the ring may be manually slid by the subject or a physician, by grabbing the ring directly or by pulling a cord connect to the ring, upon deployment. Alternatively, the ring may be configured to be slid by an actuation system on board the device. For example, a microcontroller may be pre-programmed to slide the ring at a certain time after deployment or in response to a certain detected condition, such as after delivery of the drug formulation payload.

In certain embodiments, as shown in FIG. 7, at least a portion of the retention structure, for example arms 704, may include a porous membrane 720 in fluid communication with the release end of the reservoir. In certain embodiments, the housing may also include a porous membrane sidewall 718 for distributing the drug formulations over a tissue area adjacent the porous membrane sidewall when the device is deployed in the human or animal subject.

Actuation System

In embodiments, the device includes an actuation system which is operably connected to the actuation end of the reservoir and is configured to drive the plug toward the release end to release the drug formulation from the reservoir. Generally, the actuation system is configured to drive the plug via a positive displacement process. The term "positive displacement," as used herein, refers to any process whereby the drug formulations are dispensed from the drug delivery device under force provided by the plug within the reservoir. Accordingly, the term does not refer to the passive, chemical diffusion of the drug formulations out of the reservoir, although passive diffusion may contribute to release of the drug formulations from the porous membrane. As shown in FIGS. 8A-8B, the actuation system 838 may include a power source 842, a microcontroller 844, and an actuation mechanism 846.

The power source may be any source of mechanical, electrical power or electromechanical power. The power source may include one or more batteries or fuel cells.

The microcontroller may be configured to control the actuation system of the device, and thereby control the timing of release of the drug formulations. For example, the microcontroller may selectively transmit electrical or mechanical power to the actuation mechanism, advancing the plug through the reservoir and dispensing the drug formulations. The microcontroller may be configured to control the timing of delivery of the drug formulations by applying the necessary electrical potentials to the actuation mechanism. The controller may be programmable or it may be pre-programmed to deliver the drug formulations in accordance with a prescribed release schedule.

The actuation mechanism may include fluid-volume displacement, mechanical displacement, osmotic swelling displacement, electrostatically-induced compression, piezoelectric actuation, thermally/magnetically induced phase transformation, or combinations thereof, to drive the plug via positive displacement.

In certain embodiments, as shown in FIG. 9 the actuation system 928, 929 is configured to generate a displacement fluid in operable communication with the plugs 915, 917 to drive the plugs, and the drug formulations 918, 920, toward the release end by a positive displacement process. For example, the actuation system 928, 929 may include an electrolytic cell having a cathode and an anode which contact water or an aqueous solution to generate a gas, such as oxygen, in contact with the plug. For example, the device may include actuation systems, including electrolytic cells, as described in U.S. patent application Ser. No. 13/629,159, entitled "Multiple Reservoir Drug Delivery Device and Methods," or a single reservoir as described in U.S. patent application Ser. No. 13/629,124, entitled "Single Channel, Multiple Drug Delivery Device and Methods," the disclosures of which are incorporated herein by reference in their entirety.

In one embodiment, a channel is provided in the housing to allow aqueous secretions from the mucosal tissue of the lumen to contact the cathode and anode. In one embodiment, water or an aqueous solution is contained on-board the device. For example, the actuation system may include a reservoir containing an electrolytic solution, for example an ionic solution such as sodium nitrite. In one embodiment, the actuation system includes a reservoir containing deionized water and a solid electrolyte contacting the surfaces of the cathode and anode.

An electrical potential of about 1.0 V or greater may be applied to the electrodes of the electrolytic cell to generate oxygen at the anode. In the water, at the negatively charged cathode, a reduction reaction takes place, with electrons from the cathode being given to the hydrogen cations to form hydrogen gas. The pressure exerted by the generated oxygen and hydrogen causes the plug to advance through the reservoir, thereby causing the drug formulations to be released at the release end into the lumen. The production of oxygen and hydrogen may be controlled by the power source and a microcontroller that is programmed to supply an electrical potential to the cathode and anode at a selected time.

In other embodiments, the actuation system is configured to drive the plug via positive displacement effectuated by the enlargement of a component within the actuation system, for example, a swellable material (such as a swellable gel) or an enlargeable repository. For example, the actuation system may include one or more of the actuation mechanisms as described in U.S. patent application Ser. No. 13/629,184, entitled "Drug Reconstitution and Delivery Device and Methods," the disclosure of which is incorporated herein by reference in its entirety. In some embodiments, the drug formulations are dispensed by osmotic swelling displacement. Optionally, a valve may be provided to selectively control the ingress of water into the repository or swellable material. Water from the lumen may be drawn into a repository or swellable material, causing the repository or swellable material to expand in volume. The expansion of the repository or swellable material may displace the drug formulations contained within the reservoir, causing the drug formulations to be dispensed from the device into the lumen. The actuation of the valve may be controlled by the microcontroller.

In other embodiments, the drug formulations are dispensed by an expansive force supplied by an induced phase transformation. For example, the actuation system may include an expandable repository containing a phase-transformable material. The phase-transformable material may be any liquid or solid that will undergo a phase transition from solid or liquid to gas when heated or subjected to an electro-magnetic field. When the material transforms to a gas, the material expands and advances through the reservoir to dispense the drug formulations from the device. The actuation of the phase-transformation may be controlled by the microcontroller.

In other embodiments, the drug formulations are positively displaced and dispensed from the housing by electrostatically-induced compression or using a piezoelectric actuator. For example, a dielectric elastomeric actuator or piezoelectric actuator may be arranged such that a change in voltage or current to the actuator causes the actuator to exert a compressive force on the drug formulations in the reservoir. This compressive force may cause the drug formulations to be dispensed from the device. The actuation of the actuator may be controlled by the microcontroller.

In other embodiments, positive displacement of the drug formulations is achieved using a static pressure head and an actuatable valve. The valve may be operated, for example, in an analog mode for amplitude-modulated dosing or it may be operated in a digital mode for frequency/duty-cycle modulated dosing. The static head pressure may be provided by loading the drug formulations into the device under pressure or the device may be pressurized after the drug formulations are loaded in the device.

In other embodiments, positive displacement of the drug formulations is achieved by mechanical displacement. For example, the mechanical displacement may involve a piston or a spring.

In certain embodiments, the actuation system further includes a wireless receiver for receiving wireless control signals from a separate, detached transmitting device. The device may be deployed into the lumen by the patient, physician, veterinarian, or the like, and thereafter, the patient, physician, veterinarian, or the like, may actuate the release of the drug formulations using the transmitting device to transmit control signals to the deployed device. Furthermore, in some embodiments, the receiver and transmitting device may both be transceivers capable of transmitting and receiving control signals and other communications from each other. Accordingly, in certain embodiments, the transceiver may transmit data relevant to the operation of the device, such as data regarding the drug formulations already administered, the release schedule, the amount of drug formulations remaining in the reservoir, and the remaining battery charge, as well as data relevant to the environment of the lumen, such as data detected or measured by an integral sensor. In some embodiments, the actuation system may also be wirelessly powered.

In certain embodiment, the device may is configured for wireless operation, e.g., following deployment in the human or animal subject. In such cases, the device includes appropriate telemetry components as known in the art. For example, actuation of the drug formulation dispensing may be done from a remote controller, e.g., external to the human or animal subject. Generally, the telemetry (i.e. the transmitting and receiving) is accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry systems known in the art also may be used. In another case, the device is configured to be remotely powered, or charged. For example, the device may include a transducer for receiving energy wirelessly transmitted to the device, circuitry for directing or converting the received power into a form that can be used or stored, and if stored, a storage device, such as a rechargeable battery or capacitor. In still another case, the device is both wirelessly powered and wirelessly controlled.

In some embodiments, the actuation system may further include one or more sensors for analyzing the environment around the device or within the lumen. For example, a sensor may be employed to detect the temperature or the presence of a drug-degrading enzyme in the lumen. In such embodiments, the microcontroller may be further configured to dispense the drug formulations after the abatement of the drug-degrading enzyme is detected or other suitable environmental conditions are detected for drug delivery.

Drug Formulations

One or more drug formulations are contained within the device reservoir for delivery to the mucosal tissue. Multiple drug formulations may be disposed in the reservoir in a stacked, overlapped, or other configuration. The configuration of the drug formulations within the reservoir may be determined based on the temporal release profile desired.

Various drug formulations may be administered from the drug delivery device. The different drug formulations within each reservoir may each include the same drug, may each include different drugs, or may be some combination of more than one similar drug and more than one different drug. In certain embodiments, the device may be used to deliver a battery of drug formulations for a combination therapy, prophylaxis, or for another specific treatment, such as may be useful in animal husbandry.

In one embodiment, the device is used to deliver a fixed time artificial insemination treatment to a human or animal subject. In certain embodiments, the first drug formulation includes a gonadotropin-releasing hormone, the second drug formulation includes a prostaglandin, and the third drug formulation includes a gonadotropin-releasing hormone. In one embodiment, the device also includes a fourth drug formulation which includes a progestin. Variations of the drugs and sequences are envisioned.

The drug formulations may be formulated with one or more pharmaceutically acceptable excipients as needed to facilitate the drug's storage in and release from the device. In one embodiment, the drug may be in a liquid solution or suspension. The drug may be in the form of microparticles or nanoparticles. The solvent or carrier may be aqueous or organic. For example, the devices and methods described herein may further include a reconstitution mechanism as described in U.S. patent application Ser. No. 13/629,184, entitled "Drug Reconstitution and Delivery Device and Methods," the disclosure of which is incorporated herein by reference in its entirety.

In some embodiments, the drug formulations may include components that are degradable by the enzymes present in the fluid secreted by the mucosal tissue. For example, certain amino acids present in drug formulations may be degraded by the enzymes present in fluid secreted by the mucosal tissue. Accordingly, the devices and methods described herein may further include one or more of the permeation enhancement mechanisms described in U.S. Patent Application Publications No. 2011/0087195, No. 2011/0087192, and No. 2011/0087155, the disclosures of which are incorporated herein by reference in pertinent part.

Methods

Methods are provided for transmucosal drug delivery using intraluminal devices. The intraluminal devices may include any of the device features described herein. The methods include deploying a drug delivery device into a mucosal lumen of a human or animal subject. For example, the subject may be a mammalian animal (e.g., cow, sheep, horse, pig, or dog). The methods include various medical and veterinary therapies, as well as animal husbandry applications. In particular embodiments, the mucosal lumen may be, for example, a vagina, cervix, or uterus. In other embodiments, the lumen may be a bladder or rectum. The device may be adapted to contact essentially any mucosal tissue surface. The device may be placed in the lumen by inserting the device through an exterior orifice of the patient into the lumen. Alternatively, the device may be inserted during a surgical procedure or during a laproscopic or other minimally invasive procedure.

In certain embodiments, the drug delivery device includes a housing, at least one retention member affixed to the housing, at least one reservoir within the housing having a release end and an actuation end and containing at least one drug formulation, and a plug within the at least one reservoir and moveable from the actuation end toward the release end. The retention member is transformed from a non-stressed position into a deployment position, the device is deployed into a mucosal lumen of a human or animal subject, and the retention member is transformed from the deployment position into a retention position. Thereafter, an actuation system is actuated to drive the one or more drug formulations out of the one or more reservoirs. For example, the step of actuating may include using an electrolytic cell to generate a displacement gas in communication with the plug to drive the drug formulation out of the reservoir.

As illustrated in FIG. 1B, the drug delivery device 100 may be placed in a lumen 110. The drug delivery device may be held in place by engagement between the mucosal tissue and the retention member 104, which deforms into a deployment position upon deployment and into a retention position thereafter. The drug formulation(s) may then be diffused from the release end of the reservoir via actuation of the actuation system. The actuation of the actuation system may be controlled by the microcontroller. The device may thereafter be removed from the lumen.

The method may also include distributing the drug formulation from a porous membrane sidewall in fluid communication with the release end of the at least one reservoir to a tissue area of the mucosal lumen. For example, as shown in FIG. 9, porous membrane sidewall 942 is in fluid communication with reservoirs 914, 916 and configured to distribute drug formulations 918, 920 over the lumenal tissue 926 adjacent the device. FIG. 8C illustrates how the porous membrane sidewall 840 may be incorporated into a device having retention member 804.

In certain embodiments, the retention member is transformed from the non-stressed position to into the deployment position simultaneously with deployment. For example, as shown in FIGS. 1A-1B, the transforming step may include elastically deforming two flexible arms that are substantially perpendicular to the housing in the non-stressed position, as in FIG. 1A, to be substantially parallel to the housing in the deployment position, as in FIG. 1B. The deformation may occur as a result of intraluminal forces upon deployment. Alternatively, the deformation may include a manual deformation of the retention member. Two flexible arms are shown, but other numbers (e.g., three, four, or five, etc.) of arms are envisioned.

In certain embodiments, as shown in FIGS. 2A-2B, the retention member includes three arms 204 each having a first end and a second end, the first end being affixed to the housing 202. In such embodiments, the transforming the retention member from the non-stressed position into the deployment position includes the second end being moving from a position distal the housing in the non-stressed position, as shown in FIG. 2A, to a position proximal the housing in the deployment position, as shown in FIG. 2B. Transforming the retention member from the deployment position into the retention position may include deforming the arms 204 to a position between the deployment and non-stressed positions. For example, the arms may expand out from the deployment position, but remain partially retracted due to the intraluminal forces on the device.

The methods may also include pulling a removal cord 212 connected to the arms 204 to move the second ends of the arms 204 toward the housing 202 such that the device 200 is removable from the lumen. The second ends may flex or pivot about the first ends of the arms. This feature may be augmented by forming the structural material at the first ends to be relatively thinner at a region adjacent the first ends as compared to the structural material through the remainder of the arms. The removal cord may be manually pulled by the subject or a physician to move the retention member into a retention or retracted position. Alternatively, the removal cord may be pulled by an actuation system on board the device. For example, a microcontroller may be pre-programmed to pull the removal cord at a certain time after deployment or in response to a certain detected condition.

As shown in FIGS. 3A-3B, the device may include sliding a sleeve 314 positioned about the housing 302 and slideable about the at least one arm 304 from the first end of the arm 304 toward the second end of the arm 304 to retract the arm for deployment. In one embodiment, the sleeve may be slid by pulling a removal cord 312 connected to the sleeve.

In certain embodiments, as shown in FIGS. 4A and 4B, the retention member includes a third arm 414 at an opposing end of the housing 402 from the two flexible arms 404. In such embodiments, transforming the retention member includes deforming the third arm 414 into a position such that it exerts a force on a portion of the lumen wall effective to cause a portion of the housing to contact and engage with the wall in the retention position. For example, deforming the third arm 414 may include loosening cord 412 to allow the arm 414 to expand within the lumen.

In certain embodiments, as shown in FIGS. 5A-5C and 6A-6C, the retention member includes at least one spiral member 504, 604 having a first end, a second end, and an axis 510, 610, the first end being affixed to the housing and the second end being distal to the housing such that the axis 510, 610 is parallel to the housing. In such embodiments, transforming the retention member from the non-stressed position into the deployment position includes twisting the device such that a force in generated parallel to the axis 510, 610. In one embodiment, the spiral member includes a shape memory material, such as nitinol or another material that can conform to the walls of the lumen.

In certain embodiments, as shown in FIG. 7, the device includes a tubular housing 702 and a retention sleeve having two arms 704, each arm having a first end and a second end, the first ends being affixed to the housing 702 and the second ends being affixed to a ring 716 positioned about the housing. In such embodiments, the methods include deploying the device 700 into a mucosal lumen of a human or animal subject and sliding the ring 716 to outwardly expand the two arms 704 of the retention sleeve into a retention position.

In certain embodiments, as shown in FIG. 8A-8C, the drug may be released from the housing 802 via a porous membrane 840 in fluid communication with the release end of the reservoir to a tissue area adjacent the housing 802.

As shown in FIG. 7, the drug may be distributed and released from a porous membrane in the retention member. For example, the methods may include distributing the drug formulation from the at least two arms 704 via a porous membrane 720 in fluid communication with the release end of the at least one reservoir to a tissue area adjacent the at least two arms 704.

In certain embodiments, as shown in FIGS. 10A and 10B, the housing 1002 may be transformed from a deployment position wherein the housing is straightened into a retention or non-stressed position wherein the housing is not straightened.

In one embodiment, the device may include a microcontroller. The microcontroller may actuate the release and delivery of the drug. In one embodiment, it does so by applying an electrical potential to the cathode and the anode of an electrolytic cell. For example, as gas is generated by an electrolytic cell of an actuation system, the plug is caused to advance through the reservoir, causing a drug formulation stored therein to be driven out of the reservoir. The device may thereafter be removed from the lumen.

In various embodiments, the drug delivery devices described herein may include any one or combination of the device features described herein. For example, the device may include a microcontroller configured to control the actuation system, and thereby control the timing of the release of one or more drugs, or one or more doses of the same or different drugs. Drug release may be controlled according to a preselected schedule or on demand in response to a physician or caretaker's instruction.

Applications/Uses

The drug delivery devices and methods may be used for various medical and therapeutic applications in human and animal subjects.

In some embodiments, the drug delivery device may be used to treat infertility or provide a fixed time artificial insemination (FTAI) treatment in a female subject. For example, the drug delivery device may be placed in the vagina (or uterus, or other part of the birth canal) of a female subject. The drug delivery device may then deliver follicle stimulating hormone to induce ovulation in the female subject. In some embodiments, the drug delivery device may be configured to deliver a plurality of hormones, including follicle stimulating hormone, luteinizing hormone, gonadotropin-releasing hormone separately, or in combination, in appropriate sequences, at appropriate times, and in pharmacologically appropriate amounts. The device may also dispense estradiol to regulate natural hormone production in the female subject. The appropriate dosing schedule and amounts may be determined by one in the field of reproductive pharmacology.

Compared to traditional FTAI treatments, the methods described herein require only device implantation and removal at the time of artificial insemination, and result in a reduction in time spent driving, herding and chuting cattle or other animals. The methods also result in improved ovulation quality and quantity due to the reduction in handling, stress, and systemic cortisol levels of the animals. The methods also reduce the number of medical supplies needed, as a single device delivery the series of FTAI drugs.

In another embodiment, the drug delivery device may be used to treat Type I or Type II diabetes or diabetes insipidus in a human patient. The drug delivery device may be placed within a lumen of the subject. The drug delivery device may then deliver the appropriate doses of a drug or drugs at the needed intervals.

In still other embodiments, the drug delivery device may be used to treat breast or ovarian cancer (e.g., deliver abraxane from a device inserted/retained in the vagina of a female patient), to treat osteoporosis (e.g., deliver ibandronate, calcitonin, or parathyroid hormone from a device inserted/retained in the vagina of a female patient), or to treat HIV/AIDS, genital herpes, or other sexually transmitted diseases (e.g., deliver abacavir, cidovir, or acyclovir from a device inserted/retained in the vagina of a female patient).

It will be appreciated that various of the above-disclosed and other features and functions, or alternatives thereof, may be desirably combined into many other different devices, methods, or applications. Various presently unforeseen or unanticipated alternatives, modifications, variations, or improvements therein may be subsequently made by those skilled in the art which are also intended to be encompassed by the following claims.

We claim:

1. A device for drug delivery comprising:
a housing configured for intraluminal deployment into a lumen of a human or animal subject;
at least one reservoir contained within the housing, the at least one reservoir having an actuation end and a release end and containing at least one drug formulation;
a plug within the at least one reservoir and moveable from the actuation end toward the release end;
an actuation system operably connected to the actuation end of the at least one reservoir and configured to drive the at least one drug formulation from the reservoir;
at least one retention member affixed to the housing and movable between a non-stressed position, a deployment position, and a retention position for retaining the device in an intraluminal location in the subject; and
a retention member release mechanism configured to be slideable with respect to the housing in a direction from the release end toward the actuation end to transform the retention member from the retention position to the deployment position.

2. The device of claim 1, wherein the at least one retention member is in substantially the same position in the deployment position and in the retention position.

3. The device of claim 1, wherein the at least one retention member comprises at least two flexible arms that are substantially perpendicular to the housing in the non-stressed position and substantially parallel to the housing in the deployment position.

4. The device of claim 3, wherein in the retention position, the at least two flexible arms are in a position between the non-stressed position and the deployment position.

5. The device of claim 3, wherein the at least two flexible arms are configured to be deformed from the non-stressed position to the deployment position upon intraluminal deployment.

6. The device of claim 5, wherein the at least two flexible arms are configured to be deformed from the deployment position to the retention position after intraluminal deployment.

7. The device of claim 5, wherein the at least two flexible arms are configured to be elastically deformed.

8. The device of claim 1, wherein the at least one retention member comprises at least one arm having a first end and a second end, the first end being affixed to the housing, and the second end being distal the housing in the non-stressed position and proximal the housing in the deployment position.

9. The device of claim 8, wherein in the retention position, the second end of the at least one arm is in a position between the non-stressed position and the deployment position.

10. The device of claim 8, wherein the at least one arm comprises a porous membrane in fluid communication with the release end of the at least one reservoir, the porous membrane being configured to distribute the at least one drug formulation driven from the at least one reservoir to a tissue area adjacent the at least one arm when the device is deployed in the human or animal subject.

11. The device of claim 8, wherein the at least one arm is a flexible arcuate arm configured to be deformed from the non-stressed position to the deployment position upon intraluminal deployment.

12. The device of claim 11, wherein the at least one arm is configured to be deformed from the deployment position to the retention position after intraluminal deployment.

13. The device of claim 8, further comprising at least one removal cord connected to the at least one arm and configured to move the second end of the at least one arm toward the housing upon pulling the at least one removal cord.

14. The device of claim 8, wherein the release mechanism comprises a sleeve positioned about the housing and configured to be slideable about the at least one arm such that the at least one arm assumes a retracted position adjacent the housing when the sleeve is slid from the first end of the at least one arm toward the second end of the at least one arm.

15. The device of claim 14, further comprising at least one removal cord connected to the sleeve and configured to slide the sleeve about the at least one arm and move the at least one arm from the retention position to the retracted position to facilitate insertion and removal of the device.

16. The device of claim 1, wherein the at least one retention member comprises:
two flexible arms that are substantially perpendicular to the housing in the non-stressed position and substantially parallel to the housing in the deployment position;
and a third arm at an opposing end of the housing from the two flexible arms, the third arm being configured to exert a force on a portion of the lumen such that a portion of the housing contacts a wall of the lumen in the retention position.

17. The device of claim 1, wherein the housing is pliant at one or more points such that in the non-stressed position the housing is not straightened, and in the deployment position the housing is straightened.

18. The device of claim 1, wherein the housing is configured for intravaginal or intrauterine deployment and the actuation system is configured to drive the plug and displace the at least one drug formulation.

19. A device for drug delivery comprising:
a tubular housing configured for intraluminal deployment into a human or animal subject;
at least one reservoir contained within the housing, the at least one reservoir having an actuation end and a release end and containing at least one drug formulation;
a plug within the at least one reservoir and moveable from the actuation end toward the release end;
an actuation system operably configured to drive the plug and displace the at least one drug formulation from the reservoir; and
a retention sleeve that comprises at least two arms, each arm having a first end and a second end, the first ends being affixed to the housing and the second ends being affixed to a ring positioned about the housing and slideable between a deployment position in which the at least two arms are adjacent the housing and a retention position in which the at least two arms are outwardly expanded.

20. A method of drug delivery comprising:
providing a drug delivery device that comprises:
a housing,
at least one retention member affixed to the housing, at least one reservoir within the housing, the at least one reservoir having a release end and an actuation end and containing at least one drug formulation, and a plug within the at least one reservoir and moveable from the actuation end toward the release end;

transforming the retention member from a non-stressed position into a deployment position;

deploying the device into a mucosal lumen of a human or animal subject;

transforming the retention member from the deployment position into a retention position;

actuating an actuation system to drive the plug and displace the at least one drug formulation out of the at least one reservoir while the device is retained in the mucosal lumen; and transforming the retention member from the retention position to the deployment position by moving a release mechanism along the housing in a direction from the release end toward the actuation end.

21. A method of drug delivery comprising:

providing a drug delivery device that comprises:
 a tubular housing,
 a retention sleeve having at least two arms, each arm having a first end and a second end, the first ends being affixed to the housing and the second ends being affixed to a ring positioned about the housing,
 at least one reservoir within the housing;

inserting the device into a mucosal lumen of a human or animal subject;

sliding the ring to outwardly expand the at least two arms of the retention sleeve into a retention position; and actuating an actuation system to drive the at least one drug formulation out of the at least one reservoir.

* * * * *